(12) United States Patent
Gololobov et al.

(10) Patent No.: US 11,700,870 B2
(45) Date of Patent: Jul. 18, 2023

(54) USE OF TRI- AND TETRA-SACCHARIDES AS TASTE MODULATORS

(71) Applicant: Tate & Lyle Solutions USA LLC, Hoffman Estates, IL (US)

(72) Inventors: Mikhail Gololobov, Hoffman Estates, IL (US); Joshua Fletcher, Hoffman Estates, IL (US); John Smythe, Hoffman Estates, IL (US); Ryan D. Woodyer, Hoffman Estates, IL (US)

(73) Assignee: Tate & Lyle Solutions USA LLC, Hoffman Estates, IL (US)

( * ) Notice: Subject to any disclaimer, the term of this patent is extended or adjusted under 35 U.S.C. 154(b) by 0 days.

(21) Appl. No.: 16/327,714

(22) PCT Filed: Aug. 31, 2017

(86) PCT No.: PCT/US2017/049522
§ 371 (c)(1),
(2) Date: Feb. 22, 2019

(87) PCT Pub. No.: WO2018/045122
PCT Pub. Date: Mar. 8, 2018

(65) Prior Publication Data
US 2019/0239540 A1 Aug. 8, 2019

Related U.S. Application Data

(60) Provisional application No. 62/383,022, filed on Sep. 2, 2016.

(51) Int. Cl.

| | |
|---|---|
| *A23L 2/60* | (2006.01) |
| *C07H 3/06* | (2006.01) |
| *A23L 27/00* | (2016.01) |
| *A23L 27/30* | (2016.01) |
| *A23L 33/125* | (2016.01) |
| *A23L 33/21* | (2016.01) |
| *A61K 47/26* | (2006.01) |
| *A61K 9/00* | (2006.01) |

(52) U.S. Cl.
CPC .............. *A23L 2/60* (2013.01); *A23L 27/30* (2016.08); *A23L 27/84* (2016.08); *A23L 27/86* (2016.08); *A23L 33/125* (2016.08); *A23L 33/21* (2016.08); *A61K 9/0095* (2013.01); *A61K 47/26* (2013.01); *C07H 3/06* (2013.01); *A23V 2002/00* (2013.01); *A23V 2200/16* (2013.01); *A23V 2250/28* (2013.01)

(58) Field of Classification Search
CPC . A23L 2/60; A23L 27/30; A23L 27/86; A23L 33/21; A23L 33/125; A23L 27/84; A61K 9/0095; A61K 47/26; C07H 3/06; C11D 3/221
USPC ................................................. 426/648, 548
See application file for complete search history.

(56) References Cited

U.S. PATENT DOCUMENTS

| | | | |
|---|---|---|---|
| 9,131,719 B2 | 9/2015 | Backes et al. | |
| 2004/0197453 A1 | 10/2004 | Hirao et al. | |
| 2005/0003004 A1* | 1/2005 | Vehring | A61P 9/00 264/109 |
| 2007/0128311 A1* | 6/2007 | Prakash | A61K 31/575 426/3 |
| 2010/0209585 A1* | 8/2010 | Fukuda | A23L 33/105 426/591 |
| 2013/0149383 A1* | 6/2013 | Berkland | A61K 31/09 424/490 |
| 2014/0004244 A1 | 1/2014 | Putter et al. | |
| 2015/0359251 A1 | 12/2015 | Jackson et al. | |

FOREIGN PATENT DOCUMENTS

| | | |
|---|---|---|
| CN | 101502656 | 8/2009 |
| EP | 1652527 A1 | 5/2006 |
| EP | 2340719 A1 | 7/2011 |
| EP | 2368442 A2 | 9/2011 |
| EP | 2570036 A1 | 3/2013 |
| ER | 2597082 A1 | 5/2013 |
| JP | 2005137362 A | 6/2005 |
| JP | 2007097465 A | 4/2007 |
| JP | 2013102751 A | 5/2013 |
| JP | 2014226074 A | 12/2014 |
| WO | 9833396 A1 | 8/1998 |
| WO | 2007061907 A2 | 5/2007 |
| WO | 2010080203 A1 | 7/2010 |
| WO | 2015015209 A1 | 2/2015 |
| WO | 2015015210 A1 | 2/2015 |

(Continued)

OTHER PUBLICATIONS

Hodoniczky, J., et al., "Oral and intestinal digestion of oligosaccharides as potential sweeteners: A systematic evaluation," 2012, pp. 1951-1958, vol. 132, Food Chemistry.
Chung, MY., et al., "Hypoglycemic health benefits of D-Psicose," Feb. 1, 2012, pp. 863-869, vol. 60(4), Journal of Agricultural and Food Chemistry.
Chaturvedula et al., "Acid and Alkaline Hydrolysis Studies of Stevioside and Rebaudioside A", Journal of Applied Pharmaceutical Science 01 (08); 2011—pp. 104-108.
DuBois et al., "Non-Caloric Sweeteners, Sweetness Modulators, and Sweetener Enhancers", Annu. Rev. Food Sci. Technol. 2012, 3—pp. 353-380.
Great Britain Search Report for Great Britain Application No. GB1619064.7, dated Apr. 13, 2017—3 pages.

(Continued)

*Primary Examiner* — Erik Kashnikow
*Assistant Examiner* — Bhaskar Mukhopadhyay
(74) *Attorney, Agent, or Firm* — RatnerPrestia

(57) ABSTRACT

Tri- and tetra-saccharides are used in foods, beverages and other consumable products to mask or reduce the unpleasant taste of certain components also present in such products, such as the bitter taste of certain high intensity sweeteners. The organoleptic qualities of the products are thereby improved. In particular, melezitose, maltotriose and maltotetraose effectively reduce the bitterness of consumable products containing steviol glycosides such as rebaudioside A.

23 Claims, 6 Drawing Sheets

(56) References Cited

FOREIGN PATENT DOCUMENTS

WO         2015028784 A1     3/2015
WO    WO-2015169769 A1 * 11/2015  ............. A23L 27/36
WO         2016003889 A1     1/2016

OTHER PUBLICATIONS

Wiener et al., BitterDB: A Database of Bitter Compounds Nucleic Acids Research, 2012, vol. 40, Database Issue—pp. D413-D419.

International Search Report an Written Opinion for International Application No. PCT/US2017/049522, dated Nov. 30, 2017, 17 pages.

International Preliminary Report on Patrentability for International Application No. PCT/US2017/049522, dated Mar. 5, 2019, 11 pages.

* cited by examiner

US 11,700,870 B2

USE OF TRI- AND TETRA-SACCHARIDES AS TASTE MODULATORS

CROSS-REFERENCE TO RELATED APPLICATIONS

This application is the national phase of International Application No. PCT/US2017/049522, filed Aug. 31, 2017, which claims priority to U.S. Provisional Application No. 62/383,022, filed Sep. 2, 2016, the disclosures of each of which are incorporated herein by reference in their entirety for all purposes.

FIELD OF THE INVENTION

The invention relates to compositions intended for consumption which contain one or more substances which would ordinarily impart one or more unpleasant taste sensations, such as bitterness, to the compositions, wherein at least one tri- and/or tetra-saccharide such as melezitose, maltotriose or maltotetraose is utilized to effectively block or lessen the unpleasant taste sensation(s) and provide compositions having improved taste attributes as compared to analogous compositions lacking the tri- and/or tetra-saccharide(s).

DESCRIPTION OF THE RELATED ART

Bitter blocking or masking, i.e., the reduction of bitter taste, is of great interest in the food, beverage and pharmaceutical industries to render foods, beverages, medicaments and other consumable products more palatable to the consumer. Bitter taste in general is undesirable in many types of consumable products, including, for example, products that are intended or expected to have a sweet taste (i.e., sweetened products). In recent years, there has been significant effort devoted to the development of sweeteners, both synthetic and natural, that are suitable for use as full or partial substitutes for conventional, caloric sugars (e.g., fructose, sucrose) in order to reduce the caloric and/or "sugar" content of consumable products. Non-caloric high intensity sweeteners, which are many times sweeter in taste than table sugar, are of particular interest in such applications. However, unlike conventional sugars, many of the currently available reduced- and non-caloric sugar substitutes have unpleasant taste features, e.g., off-tastes, aftertastes, bitterness and/or lingering sweetness. These unpleasant taste sensations negatively affect the overall flavor and consumer acceptability of the consumable products to which they are added. As an example, the steviol glycosides such as rebaudioside A which occur naturally in *Stevia* and *Rubus* species are considered to be desirable high intensity natural sweeteners, but when used at concentrations necessary for an adequate sweetening effect, they typically exhibit a liquorice-like and/or bitter and/or astringent taste impression. Further unpleasant taste sensations such as a long-lasting aftertaste may also be observed in consumable products formulated with one or more steviol glycosides or *Stevia* extracts. As used herein, the term "steviol glycosides" means glycosylated compounds of the ent-kaurane class of terpenoids, which typically are glycosylated derivatives of ent-kaurene or ent-kaurene.

Food and beverage products frequently contain various bitter or otherwise unpleasant-tasting substances which are characteristic of, or inherent to, such products as a consequence of their origin or which have been added to the product for some purpose (such as to sweeten the product, as mentioned above). For example, the caffeine found naturally in tea and coffee or added to certain soft drinks or energy drinks as well as the liminoids present in citrus juices are known to impart bitterness.

Thus, there exists a need for taste-masking or taste-modulating components capable of being incorporated in consumable products that can modify, modulate, mask, block, reduce and/or suppress unpleasant taste sensations attributable to certain ingredients, such as at least some types of high intensity sweeteners, which are present in such consumable products.

Various types of such taste modulators have been described in the literature. While many of these can be effective, to at least some extent, they are also recognized as having certain disadvantages. For example, while chitosan is capable of reducing the bitterness of caffeine, it is strongly astringent and thus may adversely affect the organoleptic qualities of a caffeine-containing beverage. Certain plant stanol esters, fatty acids and edible oils are also known to reduce caffeine bitterness, but likewise tend to affect other taste qualities as well and also add fat to a food product, which often may not be desirable. Ferulic acid, while capable of masking the bitterness of caffeine, adds its own distinctive taste to formulated products. Most known bitter maskants are not able to eliminate caffeine bitterness entirely.

Considerable effort has also been devoted to the development of masking agents for use in food, beverage and other products containing high intensity sweeteners, but frequently such masking agents are significantly limited in their application. For example, while caffeic acid can be employed as a masking agent, it itself has a slightly bitter taste and tends to suppress sweetness, requiring the use of a higher concentration of sweetener than would otherwise be needed. Lactisol, while exhibiting a weak bitter-reducing effect at relatively high concentrations, also at the same time suppresses the sweet taste impression. DuBois et al., "Non-Caloric Sweeteners, Sweetness Modulators, and Sweetness Enhancers," Annu. Rev. Food Sci. Technol. 2012, 3:353-380 contains a discussion of the sensory attributes associated with various high intensity sweeteners and the ongoing efforts to find ways in which the taste of such substances may be further modified and improved so as to make their sensory profiles more closely resemble that of sucrose (table sugar).

Accordingly, there remains a desire to identify additional taste modulators, especially for use in combination with high intensity sweeteners, that have improved attributes as compared to known taste modulators.

SUMMARY OF THE INVENTION

Various exemplary, non-limiting aspects of the present invention may be summarized as follows.

Aspect 1: A composition for oral ingestion comprising an edible ingredient and at least one tri- and/or tetra-saccharide (e.g., melezitose, maltotriose, maltotetraose or a combination thereof), wherein the edible ingredient has an unpleasant taste sensation (such as bitterness) when orally ingested in the absence of the at least one tri- and/or tetra-saccharide and wherein tri- and/or tetra-saccharide is present in the composition in a concentration effective to reduce or mask the unpleasant taste sensation.

Aspect 2: The composition of Aspect 1, wherein the at least one tri- and/or tetra-saccharide includes at least one of melezitose, maltotriose, maltotetraose or a combination thereof.

Aspect 3: The composition of Aspect 1, wherein the at least one tri- and/or tetra-saccharide consists essentially of at least one of melezitose, maltotriose, maltotetraose or a combination thereof.

Aspect 4: The composition of Aspect 1, wherein the at least one tri- and/or tetra-saccharide comprises at least 60%, at least 70%, at least 80%, or at least 90% by weight in total of at least one of melezitose, maltotriose, maltotetraose or a combination thereof.

Aspect 5: The composition of any of Aspects 1-4, wherein the unpleasant taste sensation is one or more of an unpleasant off-taste, an unpleasant aftertaste, lingering sweetness or bitterness.

Aspect 6: The composition of any of Aspects 1-5, wherein the unpleasant taste sensation is a bitter taste sensation.

Aspect 7: The composition of any of Aspects 1-6, wherein the edible ingredient is a high intensity sweetener.

Aspect 8: The composition of any of Aspects 1-7, wherein the edible ingredient is a high intensity sweetener selected from the group consisting of terpene glycosides (including, for example, steviol glycosides and mogrosides), glucosylated steviol glycosides, acesulfame K, saccharin, cyclamate, aspartame, sucralose, neohesperidin dihydrochalcone, and glycyrrhizin.

Aspect 9: The composition of any of Aspects 1-8, wherein the edible ingredient is a steviol glycoside.

Aspect 10: The composition of any of Aspects 1-9, wherein the edible ingredient is Rebaudioside A.

Aspect 11: The composition of any of Aspects 1-6, wherein the edible ingredient is selected from the group consisting of xanthines, alkaloids, tannins, polyphenols, quinolone derivatives, limonoids, naringin, phenolic glycosides, flavanoids, flavanoid glycosides, magnesium salts, benzoate salts, neohesperidin, active pharmaceutical ingredients, bitter amino acids and bitter peptides and peptide fragments.

Aspect 12: The composition of any of Aspects 1-11, wherein the composition is a beverage product.

Aspect 13: The composition of any of Aspects 1-12, wherein the composition is a beverage product additionally comprising water and at least one flavoring agent.

Aspect 14: The composition of any of Aspects 1-13, wherein the composition is a beverage product additionally comprising water, at least one flavoring agent and carbonation and having an acidic pH.

Aspect 15: The composition of any of Aspects 1-11, wherein the composition is a food product.

Aspect 16: The composition of any of Aspects 1-15, wherein the at least one tri- and/or tetra-saccharide (e.g., melezitose, maltotriose, maltotetraose or a combination thereof) is present in the composition at a concentration below its taste threshold concentration.

Aspect 17: The composition of any of Aspects 1-15, wherein the at least one tri- and/or tetra-saccharide (e.g., melezitose, maltotriose, maltotetraose or a combination thereof) is present in the composition at a concentration at or above its taste threshold concentration.

Aspect 18: The composition of any of Aspects 1-14, wherein the composition is a beverage product and the at least one tri- and/or tetra-saccharide (e.g., melezitose, maltotriose, maltotetraose or a combination thereof) is present at a concentration of not greater than 2.5% by weight.

Aspect 19: The composition of any of Aspects 1-14, wherein the composition is a beverage product and the at least one tri- and/or tetra-saccharide (e.g., melezitose, maltotriose, maltotetraose or a combination thereof) is present at a concentration of not greater than 10% by weight.

Aspect 20: The composition of any of Aspects 1-19, comprising from 50 ppm to 2000 ppm in total of one or more steviol glycosides.

Aspect 21: The composition of any of Aspects 1-18, comprising from 50 ppm to 2000 ppm Rebaudioside A.

Aspect 22: The composition of any of Aspects 1-11, wherein the composition is a sweetener composition and is comprised of at least one high intensity sweetener.

Aspect 23: The composition of any of Aspects 1-11 or 22, wherein the composition is a tabletop sweetener composition comprised of at least one bulking agent.

Aspect 24: A method of reducing or masking an unpleasant taste sensation (e.g., bitterness) associated with an edible ingredient (e.g., a high intensity sweetener, such as a steviol glycoside) in a composition for oral ingestion (e.g., a beverage product, a food product, a medicament), comprising formulating the composition with an effective amount of at least one tri- and/or tetra-saccharide (e.g., melezitose, maltotriose, maltotetraose, or a combination thereof).

Aspect 25: A method of making a composition for oral ingestion comprised of an edible ingredient (e.g., a high intensity sweetener, such as a steviol glycoside) which imparts an unpleasant taste sensation (e.g., bitterness) to the composition, the method comprising incorporating in the composition an amount of at least one tri- and/or tetra-saccharide (e.g., melezitose, maltotriose, maltotetraose or a combination thereof) effective to reduce or mask the unpleasant taste sensation.

Aspect 26: The method of Aspect 25, wherein the at least one tri- and/or tetra-saccharide is in the form of a mixture comprised of the at least one tri- and/or tetra-saccharide and at least one additional saccharide other than a tri- and/or tetra-saccharide.

Aspect 27: A method of sweetening a consumable product, comprising formulating the consumable product with an effective amount of the composition of Aspect 22.

Aspect 28: Use of at least one tri-saccharide (e.g., melezitose, maltotriose), at least one tetra-saccharide (e.g., maltotetraose) or a combination thereof to reduce or mask an unpleasant taste sensation (e.g., bitterness) attributable to an edible ingredient (e.g., a high intensity sweetener, such as a steviol glycoside) present in a composition for oral ingestion (e.g., a food product, a beverage product, a medicament).

Aspect 29: Use of melezitose, maltotriose, maltotetraose or a combination thereof to reduce or mask an unpleasant taste sensation (e.g., bitterness) attributable to an edible ingredient (e.g., a high intensity sweetener, such as a steviol glycoside) present in a composition for oral ingestion (e.g., a food product, a beverage product, a medicament).

DETAILED DESCRIPTION OF CERTAIN EMBODIMENTS OF THE INVENTION

Figure 1:
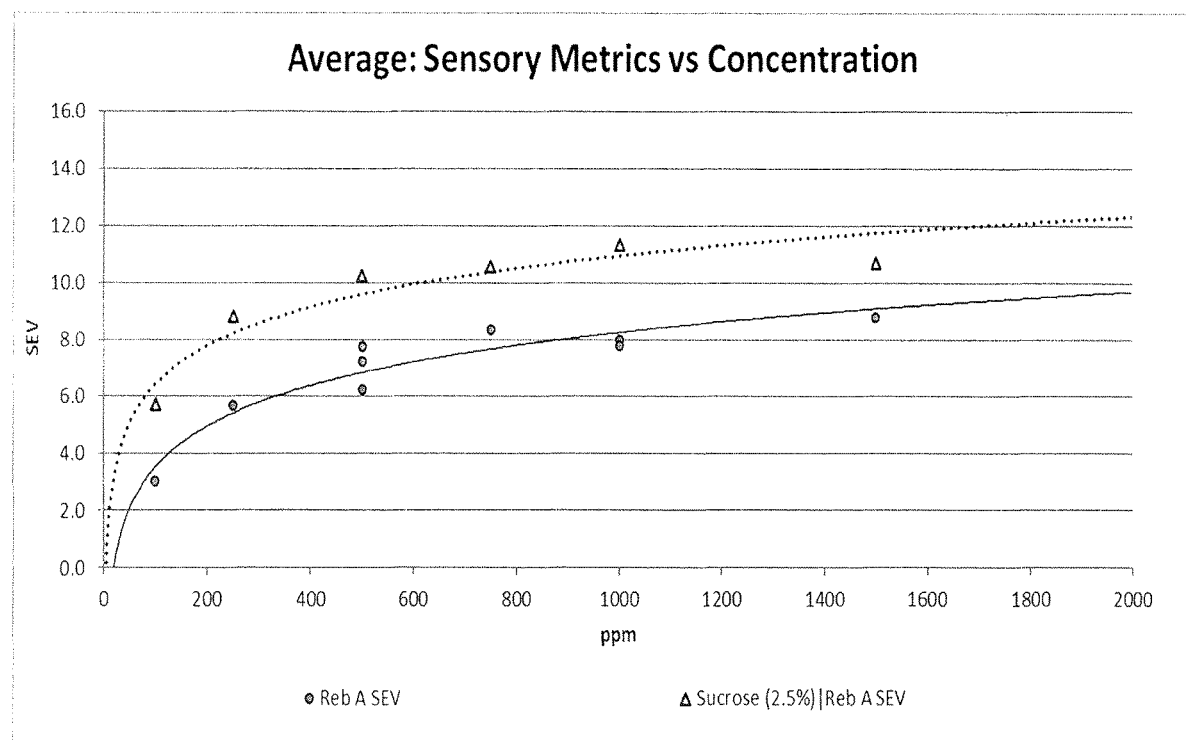
FIGS. 1-6 show dose response curves for solutions of rebaudioside A in water, solutions of rebaudioside A and melezitose in water, and solutions of rebaudioside A and sucrose in water, as further explained in the Examples.

As indicated above, there is a need for further taste-masking compositions (which may also be referred to as taste modulators) that can modify, mask (block), reduce and/or suppress unpleasant taste features associated with certain consumable product ingredients such as high intensity sweeteners (both natural and synthetic) without demonstrating disadvantages, e.g., the disadvantages of known taste-masking substances. In addition, there has been much recent interest in "natural" consumable products, e.g., products that are derived from natural sources. In some cases, because such consumable products are naturally derived, the perception of the consumer is that the products are more healthy than a similar, synthetically derived product. Accordingly, there is a desire to develop taste-masking compositions that are obtained or isolated from natural sources without chemical modification.

One of the problems underlying the present invention was to provide compositions, e.g., naturally derived compositions, which are suitable for taste-masking, in particular for modifying, masking, reducing and/or suppressing unpleasant taste features that are associated with certain consumable product ingredients such as high intensity sweeteners. For example, various unpleasant taste sensations have been associated with particular high intensity sweeteners as follows:

Saccharin: bitter and metallic off-tastes.

Cyclamate: bitter and salty off-tastes.

Acesulfame potassium: Metallic off-taste, bitter off-taste (especially at high concentrations).

Steviol glycosides: Bitter off-taste, liquorice off-taste, lingering sweetness (with some variability in these attributes existing between different individual steviol glycosides).

The present invention in one aspect, relates to the use of tri-saccharides and tetra-saccharides as taste modulators. Individual (purified) tri- or tetra-saccharides may be utilized, as can admixtures or combinations of such substances. The tri-/tetra-saccharides may be utilized to reduce or mask the above-mentioned off-tastes (unpleasant taste sensations) of particular high intensity sweeteners.

The present invention utilizes tri-saccharides and/or tetra-saccharides such as melezitose (a naturally occurring, non-reducing tri-saccharide), maltotriose and/or maltotetraose as taste modulators or maskants (maskers, blockers) in consumable products that would otherwise have certain unpleasant taste sensations due to the presence of certain components, such as certain high intensity sweeteners. The tri- and tetra-saccharides used as taste modulators in the present invention are edible (i.e., they are capable of being orally consumed without harm or injury, that is, fit for human consumption). Since, according to FDA regulations, only mono- and disaccharides are classified as "sugar," the use of a combination of a tri- or tetra-saccharide and at least one high intensity sweetener as a full or partial replacement for the mono- and/or disaccharides conventionally employed in a food or beverage product permits the tri-/tetra-saccharide-containing food or beverage product to potentially be labelled and marketed as a "low sugar" or "reduced sugar" product.

Tri-saccharides are oligosaccharides composed of three monosaccharides with two glycosidic bonds connecting them. Likewise, tetra-saccharides are oligosaccharides composed of four monosaccharides with three glycosidic bonds connecting them. Each glycosidic bond can be formed between any hydroxyl group on the component monosaccharides. The glycosidic bonds may be, for example, $\alpha(1,6)$, $\alpha(1,3)$, $\alpha(1,4)$, $\alpha(1,2)$, $\beta(1,2)$, $\beta(1,3)$, $\beta(1,4)$ or $\beta(1,6)$ or any other type of glycosidic bond; within a single tri- or tetra-saccharide, more than one type of glycosidic bond may be present. The component monosaccharides may, for example, be glucose, fructose and/or galactose.

Examples of tri-saccharides suitable for use in the present invention include, for example, isomaltotriose, nigerotriose, maltotriose, melezitose, maltotriulose, raffinose, kestose, panose and erlose and combinations of two or more of such tri-saccharides.

Melezitose is a particularly preferred tri-saccharide for use in the present invention, either as the sole tri- or tetra-saccharide, or in combination with one or more other tri- and/or tetra-saccharides. Melezitose is also referred to by the chemical name $\alpha$-D-glucose (1-3)-$\beta$-D-fructose (2-1)-$\alpha$-D-glucose and has the empirical formula $C_{18}H_{32}O_{16}$. Melezitose has been assigned CAS #10030-67-8 and has a molecular weight of 504.44 Da. This tri-saccharide can be considered as fructose substituted with two glucose residues, or as turanose (an isomer of sucrose) substituted with glucose, or as sucrose substituted with glucose. Melezitose can be partially hydrolyzed to glucose and turanose, is readily soluble in water (e.g., 26.8 g of melezitose dissolves in 100 g water at 21° C.), and has a slightly sweet taste. The melting point of melezitose is reported to be 153-154° C.; the glass transition temperature of melezitose is approximately 60° C.

Examples of tetra-saccharides suitable for use in the present invention include, for example, lychnose (1-$\alpha$-galactosyl-raffinose), maltotetraose, nigerotetraose, nystose ($\beta$-D-fructosyl-kestose), sesamose, stachyose and combinations thereof.

The use of melezitose in particular as a taste modulator or maskant in accordance with the present invention is advantageous because, unlike most other tri- and tetra-saccharides, it has been found in recent studies not to be digestible by in vitro assay and also not utilized by *S. mutans* in dental caries assay (Oral and intestinal digestion of oligosaccharides as potential sweeteners: A systematic evaluation. Hodoniczky et. al. Food Chemistry 132 (2012) 1951-1958).

Stachyose is also of particular interest for use as a taste modulator or maskant in accordance with the present invention, since it also has a low degree of digestibility as compared to sucrose. The caloric content of stachyose has been estimated to be 1.5-2.4 Kcal/g; it is approximately 28% as sweet as sucrose on a weight basis. Stachyose is present in artichokes and certain types of beans such as soybeans and green beans.

Any of the above-mentioned tri- and tetra-saccharides may be used in combination. Alternatively a single tri- or tetra-saccharide may be utilized.

The tri- and tetra-saccharide(s) utilized in the present invention may be obtained from any suitable source, e.g., it may be isolated from natural sources or prepared biosynthetically. Melezitose, for example, is produced by many plant sap-eating insects, including aphids such as *Cinara pilicornis* by an enzyme reaction. This process is beneficial to the insects, as it reduces the osmotic effects of high-sucrose diets by converting sucrose to oligosaccharides. The melezitose is part of the excreted "honeydew" which acts as an attractant for ants and also as a food for bees. This is useful to the aphid as they have a symbiotic relationship with ants.

Melezitose is a natural component of honey, and is ordinarily present in low amounts. However, occasionally bees will take sugars from honeydew and larger amounts of the tri-saccharide will accumulate in the honey. Honeydew honey compared to blossom honey contains higher amounts of oligosaccharides, and also tri-saccharides such as melezitose and raffinose.

Melezitose honey or "cement honey" is a granulated honey with very high content of melezitose. This cement honey can be harvested only with great difficulty or not be harvested at all, but can be processed to isolate the melezitose it contains. Melezitose also can be obtained by simple aqueous extraction from plant sources. The melezitose used in the compositions of the present invention can alternatively be produced by the enzymatic transglucosylation of sucrose. Enzymes capable of performing this transformation are present in the gut of several insects and in a number of plants.

For example, an α-glucosidase/transglucosidase enzyme ("APS1", EC3.2.1.20) has been cloned from an insect (pea aphid, *Acryrthosiphon pisum*); this enzyme may be responsible for the biosynthesis of melezitose by the insect. This enzyme or an enzyme having a similar activity may be used for biosynthesis of melezitose from sucrose.

In addition, honey contains an α-glucosidase enzyme derived from the hypopharyngeal gland of the honey bee (*Apis mellifera* L.). Some fraction of the oligosaccharides in honey may be derived from the transglycosylation (reversion) of honey sugars by this enzyme. The enzyme has been cloned and expressed in the yeast *Pichia pastoris* and could potentially be employed in the production of melezitose.

Tri- and tetra-saccharides are commercially available or can be prepared by the skilled person based on his or her general knowledge. For example, tri- and tetra-saccharides may be prepared by hydrolysis (hydrolytic cleavage) of longer chain oligosaccharides and polysaccharides catalyzed by enzymes such as amylase and pullulanase enzymes, particularly enzymes having high DP3+4 selectivity. The hydrolysis reaction products may be further fractionated or purified to isolate individual tri- and tetra-saccharides or to obtain products enriched in DP3 and/or DP4 content. For example, starch may be hydrolyzed using maltotriose- or maltotetraose-producing amylases to provide reaction products containing maltotriose and/or maltotetraose.

An alternative approach is to synthesize tri- and tetra-saccharides by linking together shorter chain length saccharides such as mono- and di-saccharides (e.g., glucose, fructose, galactose, sucrose, turanose; certain enzymes may be used to catalyze such linking reactions and/or to favor selectivity to certain particular types of tri- and tetra-saccharides. Suitable tri- and tetra-saccharides may be of synthetic or, preferably, of natural origin.

In various embodiments of the invention, the at least one tri- and/or tetra-saccharide may comprise, consist essentially of, or consist of melezitose. That is, melezitose may constitute part of, including a majority of, the total amount of tri- and/or tetra-saccharide present in a consumable composition or a sweetener composition or used to sweeten or modulate the taste of a consumable composition. For example, melezitose may represent at least 50%, at least 60%, at least 70%, at least 80%, at least 90%, at least 95%, at least 99% or even 100% by weight of the total amount of tri- and tetra-saccharide.

In other embodiments of the invention, the at least one tri- and/or tetra-saccharide may comprise, consist essentially of, or consist of maltotriose, maltotetraose or a combination thereof. That is, maltotriose and/or maltotetraose may constitute part of, including a majority of, the total amount of tri- and/or tetra-saccharide present in a consumable composition or a sweetener composition or used to sweeten or modulate the taste of a consumable composition. For example, at least 50%, at least 60%, at least 70%, at least 80%, at least 90%, at least 95%, at least 99% or even 100% by weight of the total amount of tri- and tetra-saccharide may be maltotriose, maltotetraose or a combination of maltotriose and maltotetraose.

In other embodiments of the invention, a tri- and/or tetra-saccharide (or combination of different tri- and tetra-saccharides) is utilized which has a caloric content less than that of sucrose, e.g., less than 4 kcal/g, less than 3.5 kcal/g, less than 3 kcal/g, less than 2.5 kcal/g, less than 2 kcal/g, less than 1.5 kcal/g or even less than 1 kcal/g per gram. The caloric content of a tri-/tetra-saccharide may be measured using the procedures described in Chung, Min-Yu; Oh, Deok-Kun; Lee, Ki Won (1 Feb. 2012). "Hypoglycemic health benefits of D-psicose". *J Agric Food Chem. ACS.* 60 (4): 863-869. The structure of the tri- and/or tetra-saccharide(s) may be selected such that it is more resistant to digestion and metabolism when orally consumed by a human than sucrose. For example, the types of glycosidic bonds between the monosaccharide units of the tri-/tetra-saccharide may be chosen to be resistant to hydrolytic cleavage under the conditions present in the human digestive system. Alpha linkages are generally more easily cleaved than beta linkages, for instance, and α(1,4) glycosidic bonds are generally more susceptible to hydrolysis catalyzed by enzymes present in the human digestive system than are α(1,6) glycosidic bonds.

In certain embodiments of the invention, a saccharide source predominantly comprised of tetrasaccharide (e.g., maltotetraose) but also comprising trisaccharide (e.g., maltotriose) and relatively minor amounts of other saccharides (e.g., monosaccharides, disaccharides, maltopentaose and/or higher oligosaccharides) is used as a maskant or taste modulator. Saccharide sources useful for such purpose may, for example, have the following saccharide distributions, expressed on a dry weight basis (the total equaling 100% for each of Embodiments A-D):

| General Type of Saccharide | Exemplary Saccharide | Embodiment A | Embodiment B | Embodiment C | Embodiment D |
| --- | --- | --- | --- | --- | --- |
| Monosaccharide (DP1) | Glucose | 1-12% | 8-12% | 1-3% | 4-6% |
| Disaccharide (DP2) | Maltose | 1-12% | 8-12% | 1-3% | 4-6% |
| Trisaccharide (DP3) | Maltotriose | 5-20% | 7-10% | 12-18% | 9-11% |
| Tetrasaccharide (DP4) | Maltotetraose | 55-75% | 65-70% | 68-72% | 68-72% |
| Pentasaccharide and higher (DP5+) | Maltopentaose and higher maltooligosaccharides | 1-20% | 5-15% | 5-15% | 5-15% |

It has now been surprisingly and unexpectedly found that at least certain tri- and tetra-saccharides, and melezitose, maltotriose and maltotetraose in particular, are useful for taste-masking, in particular for modifying, masking, reducing and/or suppressing unpleasant taste features, in particular bitterness or an unpleasant off-taste or aftertaste (e.g., a lingering sweetness), left by certain consumable product ingredients (i.e., "edible ingredients") such as high intensity sweeteners in the oral cavity. The effect of the tri-/tetra-saccharide may remain as long as the taste of the at least one consumable product ingredient (e.g., high intensity sweetener) is perceived. In one embodiment, the effect of the tri- or tetra-saccharide (e.g., melezitose, maltotriose, maltotetraose) does not remain any longer than the taste of the at least one consumable product ingredient is perceived, i.e., the tri-/tetra-saccharide does not have a lingering effect.

In various embodiments of the invention, the consumable product ingredient (edible ingredient) which, in the absence of a tri-/tetra-saccharide maskant or taste modulator, tends to impart at least one unpleasant taste sensation to a consumable product in which it is present at a desired or preselected concentration. High intensity sweeteners, which are described in more detail below, are one type of such consumable product ingredient. However, the consumable product ingredient may be any edible ingredient other than a high intensity sweetener. Illustrative, non-limiting examples of such consumable product ingredients include xanthines (also referred to as xanthine alkaloids, e.g., caffeine, theobromine), alkaloids, tannins, polyphenols (e.g., catechols, flavanols, hesperitin), quinolone derivatives (e.g., quinine, quinine salts), limonoids (for example limonine from citrus fruits), naringin, phenolic glycosides, flavanoids, flavanoid glycosides, magnesium salts (e.g., magnesium sulfate), benzoate salts (e.g., sodium benzoate), neohesperidin, active pharmaceutical ingredients, bitter amino acids (e.g., tryptophan) and bitter peptides and peptide fragments.

Consumable products which are improved in taste in accordance with the present invention may contain more than one ingredient which provides, in the absence of a maskant, an unpleasant taste sensation to the consumable product when orally consumed. For example, a consumable product may contain both a high intensity sweetener and an ingredient which is not a high intensity sweetener, each of which adversely affects the taste of the consumable product in some way. The edible ingredient or ingredients having a taste in need of masking may be inherently present in a food (such as certain of the bitter-tasting substances present in coffee, processed cacao or fruit or vegetable juices) or may be added as separate ingredients to prepare a formulated consumable product (such separate ingredients typically being used to impart some desired characteristic). A database of compounds known to be bitter-tasting may be found at Ayana Wiener; Marina Shudler; Anat Levit; Masha Y. Niv. BitterDB: a database of bitter compounds. Nucleic Acids Res 2012, 40(Database issue):D413-419.

As used herein, the term "taste-masking" as it relates to the tri-/tetra-saccharide means that the tri-/tetra-saccharide imparts an improvement in a taste profile of a composition, e.g., for example the taste profile of a sweetener composition, tabletop sweetener composition and/or a consumable product composition. Preferably, taste-masking is perceived as a modification, masking, reduction and/or suppression of an unpleasant off-taste, aftertaste or lingering sweetness in the oral cavity that may be left by sweeteners or sweetness enhancers. Taste-masking may also be perceived as imparting rich taste to a consumable product. In some instances, for example, the taste-masking may be perceived as a reduction or masking of the bitterness of a sweetener composition or of a beverage or foodstuff containing the sweetener composition. In other instances, the taste-masking may also be perceived as an enhancement in the sweetness of a sweetener composition or of a beverage or foodstuff containing the sweetener composition. The taste-masking may also be a combination of both bitterness reduction and sweetness enhancement.

As used herein, the term "modifying" as it relates to the tri-/tetra-saccharides described above means that consumption thereof creates a new perception of taste, off-taste, aftertaste or lingering sweetness of a sweetener composition or a consumable product in the oral cavity.

As used herein, the term "masking" as it relates to the tri-/tetra-saccharides described above means that consumption thereof masks a perception of a taste, off-taste, aftertaste or lingering sweetness of a sweetener composition or a consumable product in the oral cavity.

As used herein, the term "reducing" as it relates to tri-/tetra-saccharides as described above means that consumption thereof reduces a perception of a taste, off-taste, aftertaste or lingering sweetness of a sweetener composition or a consumable product in the oral cavity.

As used herein, the term "suppressing" as it relates to tri-/tetra-saccharides as described above means that consumption thereof suppresses a perception of a taste, off-taste, aftertaste or lingering sweetness of a sweetener composition or a consumable product in the oral cavity.

As used herein, the term "off-taste" means any taste of a sweetener or a consumable product, e.g., a food or beverage, that is perceived in the oral cavity on or after consumption thereof and that can stay there for a few minutes. Off-tastes include but are not limited to acidic, astringent, bitter, liquorice, metallic or throat-burning.

As used herein, the term "aftertaste" means any taste of a sweetener or a consumable product, e.g., a food or beverage, that is perceived in the oral cavity after the sweetener or the consumable product is removed from the oral cavity, e.g., by swallowing or disgorging. The aftertaste may remain in the oral cavity for example, for a few minutes or a few hours. Unpleasant aftertastes include but are not limited to bitter and/or astringent aftertastes. In one embodiment, the aftertaste is provided by a high intensity sweetener such as acesulfame potassium, saccharin and/or terpene glycoside (e.g., a steviol glycoside or mogroside).

As used herein, the term "lingering sweetness" means a very long-lasting sweetening effect of a sweetener or a consumable product, e.g., a food or beverage, which is perceived in the oral cavity after the sweetener or the consumable product is removed from the oral cavity by swallowing or disgorging. The lingering sweetness may remain in the oral cavity for example, for a few minutes or a few hours.

As used herein, the term "rich taste" means an impression of creaminess, milk fattiness and/or sweetness of a consumable product that is perceived in the oral cavity on or after consumption of a consumable product.

As used herein, the term "sweetener(s)" includes all artificial (synthetic) and natural sweeteners, sugar alcohols (or polyols) and sugar sweeteners (or carbohydrates), including high intensity sweeteners (sweeteners having a greater sweetness than sucrose). The sweetener may be a caloric sweetener and/or a non-caloric sweetener. The sweetener may be a caloric sweetener that has a caloric content that is less than that of sugar (sucrose). Artificial (synthetic) and natural sweeteners include, but are not limited to, abiziasaponin, abrusosides, in particular abrusoside A, abrusoside B, abrusoside C, abrusoside D, acesulfame potassium, advantame, albiziasaponin, alitame, aspartame, superaspartame, bayunosides, in particular to bayunoside 1, bayunoside 2, brazzein, bryoside, bryonoside, bryonodulcoside, carnosifloside, carrelame, curculin, cyanin, chlorogenic acid, cyclamates and its salts, cyclocaryoside I, dihydroquercetin-3-acetate, dihydroflavenol, dulcoside, gaudichaudioside, glycyrrhizin, glycyrrhetin acid, gypenoside, hematoxylin, hernandulcin, isomogrosides, in particular iso-mogroside V, lugduname, magap, mabinlins, miraculin, mogrosides (as found in Luo Han Guo fruit and extracts thereof), in particular mogroside IV and mogroside V, monatin and its derivatives, monellin, mukurozioside, naringin dihydrochalcone (NarDHC), neohesperidin dihydrochalcone (NDHC), neotame, osladin, pentadin, periandrin I-V, perillartine, D-phenylalanine, phlomisosides, in particular phlomisoside 1, phlomisoside 2, phlomisoside 3, phlomisoside 4, phloridzin, phyllodulcin, polpodiosides, polypodoside A, pterocaryosides, rebaudiosides, in particular rebaudioside A, rebaudioside B, rebaudioside C, rebaudioside D, rebaudioside E, rebaudioside F, rebaudioside G, rebaudioside H, rebaudioside M (X), rebaudioside N, rebaudioside O), rubusosides, saccharin and its salts and derivatives, scandenoside, selligueanin A, siamenosides, in particular siamenoside I, *Stevia* extracts, steviolbioside, stevioside and other steviol glycosides (including rebaudiosides), glucosylated steviol glycosides (also referred to as enzyme-treated or enzyme-modified steviol glycosides), strogines, in particular strogin 1, strogin 2, strogin 4, suavioside A, suavioside B, suavioside G, suavioside H, suavioside I, suavioside J, sucralose, sucronate, sucrooctate, talin, telosmoside $A_{15}$, thaumatin, in particular thaumatin I and II, trans-anethol, trans-cinnamaldehyde, trilobtain and D-tryptophane, including extracts or enriched fractions of the natural sweeteners. Sugar alcohols (or polyols) include but are not limited to erythritol, galactitol, hydrogenated starch syrups including maltitol and sorbitol syrups, inositols, isomalt, lactitol, maltitol, mannitol, xylitol, and combinations thereof. Sugar sweeteners (or carbohydrates) include monosaccharides, disaccharides, oligosaccharides and polysaccharides such as but not limited to arabinose, dextrin, dextrose, fructose, high fructose corn syrup, fructooligosaccharides, fructooligosaccharide syrups, galactose, galactooligosaccharides, glucose, glucose and (hydrogenated) starch syrups/hydrolysates, isomaltulose, lactose, hydrolysed lactose, maltose, mannose, rhamnose, ribose, sucrose, stachyose, tagatose, trehalose, xylose, allulose (psicose), allose and combinations thereof, including all isomers thereof (e.g., D and L isomers). Sweeteners based on extracts of *Stevia* leaves, which may be purified or fractionated to various degrees, are particularly suitable for use, as are terpene glycosides (e.g., sweet steviol glycosides, mogrosides), isolated from natural sources. The above-identified sweeteners are known in the art and many are commercially available.

In one embodiment, the sweetener comprises, consists essentially of or consists of one or more steviol glycosides. For example, the sweetener may comprise at least 50%, at least 60%, at least 70%, at least 80%, at least 90%, at least 95% or at least 99% by weight steviol glycoside, including one or more of the steviol glycosides mentioned above.

In another embodiment, the sweetener comprises, consists essentially of or consists of rebaudioside A. For example, the sweetener may comprise at least 50%, at least 60%, at least 70%, at least 80%, at least 90%, at least 95% or at least 99% by weight rebaudioside A; the balance, if any, of such a sweetener may be comprised of one or more other steviol glycosides, including any of those mentioned above.

Thus, in one aspect, the invention relates to the use of tri-/tetra-saccharide(s) as described above for modifying, masking, reducing and/or suppressing an unpleasant taste feature, in particular an unpleasant off-taste, aftertaste or lingering sweetness of at least one sweetener or a consumable product.

Preferably, the effect of the tri-/tetra-saccharide(s) remains at least as long as the taste of the at least one sweetener or the consumable product is perceived.

In one embodiment, the unpleasant off-taste of the sweetener or a consumable product is an acidic off-taste, an astringent off-taste, a bitter off-taste, a liquorice off-taste, a metallic off-taste or a throat-burning off-taste.

In one embodiment, the unpleasant aftertaste of the sweetener or the consumable product is an astringent or bitter aftertaste.

In another embodiment, the invention relates to the use of a tri-/tetra-saccharide or combination thereof as described above for imparting rich taste to a consumable product.

Sweetener Compositions

It has now been found that sweetener compositions comprising one or more tri-/tetra-saccharides (especially melezitose, maltotriose, maltotetraose or a combination thereof) as described above are useful in 1) reducing the quantity of a standard sugar such as sucrose that may be present in a consumable product; and/or in 2) replacing a standard sugar such as sucrose that may be present in a consumable product.

In another aspect, the invention relates to a sweetener composition comprising (a) at least one sweetener (as described above); and (b) at least one tri-/tetra-saccharide (melezitose, maltotriose, and/or maltotetraose in particular) as described above.

In one embodiment, the sweetener composition comprises at least one artificial or natural sweetener (or combination of at least one artificial sweetener and at least one natural sweetener) that, once consumed, is capable of leaving an unpleasant off-taste, aftertaste or lingering sweetness in the oral cavity.

Exemplary artificial or natural sweeteners include but are not limited to abiziasaponin, abrusosides, in particular abrusoside A, abrusoside B, abrusoside C, abrusoside D, acesulfame potassium, advantame, albiziasaponin, alitame, aspartame, superaspartame, bayunosides, in particular bayunoside 1, bayunoside 2, brazzein, bryoside, bryonoside, bryonodulcoside, carnosifloside, carrelame, curculin, cyanin, chlorogenic acid, cyclamate and its salts, cyclocaryoside I, dihydroquercetin-3-acetate, dihydroflavenol, dulcosides, gaudichaudioside, glycyrrhizin, glycyrrhetin acid, gypenoside, hematoxylin, hernandulcin, isomogrosides, in particular iso-mogroside V, lugduname, magap, mabinlins, miraculin, mogrosides (obtainable from Luo Han Guo fruit), in particular mogroside IV and mogroside V, monatin and its derivatives, monellin, mukurozioside, naringin dihydrochalcone (NarDHC), neohesperidin dihydrochalcone (NDHC), neotame, osladin, pentadin, periandrin I-V, perillartine, D-phenylalanine, phlomisosides, in particular phlomisoside 1, phlomisoside 2, phlomisoside 3, phlomisoside 4, phloridzin, phyllodulcin, polpodiosides, polypodoside A, pterocaryosides, rebaudiosides, in particular rebaudioside A, rebaudioside B, rebaudioside C, rebaudioside D, rebaudioside E, rebaudioside F, rebaudioside G, rebaudioside H, rebaudioside M (X), rebaudioside N, rebaudioside O and glucosylated derivatives thereof), rubusosides, saccharin and its salts and derivatives, scandenoside, selligueanin A, siamenosides, in particular siamenoside I, *Stevia* extracts, steviolbioside, stevioside and other steviol glycosides and glucosylated derivatives thereof, strogines, in particular strogin 1, strogin 2, strogin 4, suavioside A, suavioside B, suavioside G, suavioside H, suavioside I, suavioside 3, sucralose, sucronate, sucrooctate, talin, telosmoside $A_{15}$, thaumatin, in particular thaumatin I and II, trans-anethol, trans-cinnamaldehyde, trilobtain and D-tryptophane, including extracts or enriched fractions of the natural sweeteners. The above-identified sweeteners are known in the art and are commercially available. Any of the aforementioned sweeteners may be used in combination in any relative proportions.

Extracts or enriched fractions of natural sweeteners may include extracts with more than 10 wt %, preferably with more than 50 wt % and more preferably with more than 90 wt % of the sweetener concerned in relation to the dry mass of the fraction.

In one embodiment, the amount of the tri-/tetra-saccharide(s) (e.g., melezitose, maltotriose, maltotetraose or a combination thereof) in the sweetener composition is such that when the sweetener composition is added to a consumable product, the amount of said tri-/tetra-saccharide(s) is below its/their taste threshold concentration, i.e., the presence of the tri-/tetra-saccharide(s) cannot be identified and/or recognized in the consumable product when consumed.

In another embodiment, the amount of the tri-/tetra-saccharide(s) (e.g., melezitose, maltotriose, maltotetraose or a combination thereof) in the sweetener composition is such that when the sweetener composition is added to a consumable product, the amount of said tri-/tetra-saccharide(s) is at or above their taste threshold concentration, i.e., the presence of the tri-/tetra-saccharide(s) can be identified in the consumable product when consumed. Typically, the tri- and tetra-saccharides useful in the present invention as taste modulators have some degree of sweetness, when tasted at a relatively high concentration, although generally a lower sweetness intensity than sucrose. Accordingly, the tri-/tetra-saccharide(s) can help impart a sweet taste to the consumable product, in addition to the sweetness contributed by other components of the sweetener composition (e.g., a high intensity sweetener). The tri-/tetra-saccharide(s), due to their generally lower sweetness intensity as compared to sucrose, may additionally function as bulking agents in the consumable product when used in relatively high concentrations, in addition to helping to mask or reduce one or more unpleasant taste sensations attributable to one or more other ingredients in the consumable product (such as a high intensity sweetener, for example).

In various embodiments, the tri-/tetra-saccharide(s) (e.g., melezitose, maltotriose, maltotetraose or a combination thereof) as described above is/are present in the sweetener composition in an amount effective to modify, mask, reduce and/or suppress an unpleasant off-taste, aftertaste or lingering sweetness of the at least one sweetener, wherein the amount is less than, equal to or greater than a taste threshold concentration associated with the tri-/tetra-saccharide(s) (e.g., melezitose, maltotriose, maltotetraose or a combination thereof).

In one embodiment, the effect of the tri-/tetra-saccharide(s) (e.g., melezitose, maltotriose, maltotetraose or a combination thereof) remains at least as long as the taste of the at least one sweetener is perceived.

As used herein, the term "taste threshold concentration associated with the tri-/tetra-saccharide(s)" means the minimum concentration at which a person can still taste the tri-/tetra-saccharide(s) by the human sense of taste, in particular in an aqueous solution containing no ingredient other than water and the tri-/tetra-saccharide(s). This taste threshold concentration may vary somewhat from person to person. For example, melezitose has a taste threshold concentration of about 2.5% by weight in a neutral aqueous solution containing no other ingredients.

Based on the description of the tri-/tetra-saccharide(s) as described above, a person skilled in the art will be able to select the amount effective to modify, mask, reduce and/or suppress an unpleasant off-taste, aftertaste or lingering sweetness of the at least one sweetener, wherein the amount is less than, equal to or greater than a taste threshold concentration associated with the tri-/tetra-saccharide(s).

The sweetener composition may take any suitable form including, but not limited to, an amorphous solid, a crystal, a powder, a tablet, a liquid (e.g., a syrup), a cube, a glaze or coating, a granulated product, an encapsulated form, a form in which the sweetener composition is bound to or coated on to carriers/particles, or combinations thereof. In one embodiment of the invention, the sweetener composition of the invention is liquid at ambient conditions. In another embodiment of the invention, the sweetener composition of the invention is solid at ambient conditions.

The sweetener composition or the consumable product composition of the present invention may contain further additives or ingredients known to those skilled in the art. These additives include, but are not limited to, dust control agents, bubble forming agents, surfactants, emulsifiers, fats, gums, hydrocolloids, bulking agents, carriers, fibers, flavoring ingredients, flavor enhancers, stabilizers, preservatives, sweetness enhancers, acidulants and other pH adjusting agents, buffers, anti-caking and free-flow agents.

In one embodiment, the invention relates to a sweetener composition in the form of a solution, e.g., a sweetener composition solution, comprising at least one solvent, at least one sweetener and the tri-/tetra-saccharide(s). Preferably, the solvent is or may include water and/or another polar solvent such as an alcohol that may be safely consumed (e.g., ethanol, glycerol, propylene glycol). Furthermore, the solvent, in particular water, may comprise one or more consumable buffers (e.g., a citrate buffer). The sweetener composition solution may be in the form of a syrup or concentrate having a relatively high concentration of ingredients other than solvent, wherein such ingredients are fully dissolved in the solvent (e.g., water). Sweetener compositions in the form of dispersions or suspensions, wherein at least a portion of at least one ingredient of the sweetener composition remains undissolved but suspended or dispersed in a liquid carrier solvent (e.g., water and/or consumable organic solvent) are also considered to be within the scope of the present invention.

In one embodiment, the tri-/tetra-saccharide(s) are present in the sweetener composition solution in an amount such that, when the solution is added to a consumable product, the flavor or taste of the sweetener (in the consumable product) is improved, as compared to a similar consumable product comprising the sweetener but not comprising the tri-/tetra-saccharide(s).

In one embodiment, the sweetener composition solution comprises the tri-/tetra-saccharide(s) and the sweetener and the tri-/tetra-saccharide(s) are present in the solution in an amount such that, when the solution is added to a consumable product, the tri-/tetra-saccharide(s) is/are not detectable by taste in the consumable product.

In one embodiment, the sweetener composition solution may be processed to inactivate microorganisms that may be present in the solution. The processing step may vary widely. Many suitable processing steps are known in the art. For example, the solution may be subjected to UV treatment, microfiltration, pasteurization, and combinations thereof.

This listing is merely exemplary and is not meant to limit the scope of potential processing steps.

In various embodiments, the sweetener composition has a sweetness intensity that is at least 10, at least 50 or at least 100 times greater than the sweetness intensity of sugar (sucrose). In such embodiments, the sweetener composition generally will contain at least one high intensity sweetener, either natural or synthetic, such as a steviol glycoside (e.g., a rebaudioside such rebaudioside A or a mixture of steviol glycosides, such as may be provided in the form of a *Stevia* extract), aspartame, acesulfame K, saccharin or sucralose. For example, a 1 g portion of the sweetener composition may be at least 10, at least 50 or at least 100 times sweeter than a 1 gram portion of granulated sugar (meaning that a relatively small amount of the sweetener composition needs to be incorporated into a consumable product in order to impart to that consumable product a level of sweetness equivalent to that provided by a larger amount of sucrose). This makes it possible to formulate consumable products having a reduced amount of sugar and a reduced caloric content as compared to an analogous conventional consumable product which is made using sucrose or other caloric saccharide as a sweetener.

The taste of the sweetener composition with regard to sweetness and/or sweetness enhancing properties and/or other tastes, in other embodiments, may be assessed in vivo by using a panel of trained sensory evaluators experienced in the sweet taste estimation procedure, e.g. in a taste and spit assay.

The taste-masking properties of the tri-/tetra-saccharide(s) as described above, e.g., the effectiveness of the tri-/tetra-saccharide(s) as described above for modifying, masking, reducing and/or suppressing an unpleasant off-taste, aftertaste or lingering sweetness of the at least one sweetener in the sweetener composition may also be assessed using a taste and spit assay.

A taste and spit assay may also be used for assessing whether the effect of the tri-/tetra-saccharide(s) remains at least as long as the taste of the at least one sweetener is perceived. A taste and spit assay may also be used in the analyses of other taste-related determinations and/or assessments.

In these cases, panelists are asked to take a sample of the liquid to be assessed, e.g., the sweetener composition comprising tri-/tetra-saccharide(s) as described above, into the mouth and after some time allowed for taste perception to spit the sample out completely. Subsequently, the panelists are asked to rinse their mouth well with water or other liquid to reduce any potential carry over effects. The tasting of a sample can be repeated if required.

In a first descriptive test (qualitative assessment of the sweetener composition comprising the tri-/tetra-saccharide(s) as described above for sweetness, off-taste, aftertaste and/or lingering sweetness) the panelists are asked to taste the quality of single samples (maximum 3 subsequent samples). The individuals of the taste panel are asked to answer the following questions with regard to the quality of taste: 1) does the sample taste sweet?, 2) is there another taste detectable (e.g. bitter, sour, salty, metallic, etc.)?, 3) is there any off- or aftertaste or lingering sweetness?, 4) is there anything else remarkable in the perception of the sample (e.g. rich taste)?

In a second test (qualitative assessment for taste masking properties of the tri-/tetra-saccharide(s) as described above) the panelists are asked to answer questions in a pairwise comparison test to determine the taste-masking properties of the tri-/tetra-saccharide(s) as described above. In this test the taste of the sweetener composition comprising the tri-/tetra-saccharide(s) as described above is pairwise compared to the taste of the respective sweetener composition without the tri-/tetra-saccharide(s) as described above. Again the panelists are given samples. Two samples are prepared for direct comparison regarding sweetness, off-taste, aftertaste and lingering sweetness.

One sample contains the sweetener composition without the tri-/tetra-saccharide(s) as described above in a solvent. The other sample contains the sweetener composition comprising the tri-/tetra-saccharide(s) as described above. Designation of the samples with A and B is randomized and is decoded after the taste procedure. The questions to be answered are: 1) does one sample taste sweeter than the other?, 2) if so, which one?, 3) are there any other differences in the taste between the two samples? The result of the taste and spit assay is a qualitative evaluation of the differences between the two samples.

Methods of Making a Sweetener Composition

In another aspect, the present invention relates to a method of making a sweetener composition, comprising the step of combining with at least one sweetener at least one tri- and/or tetra-saccharide(s) as described above (in particular, melezitose) and, optionally, one or more additional additives or ingredients (e.g., bulking agent, carrier, flavors) to yield a sweetener composition. As a result, the sweetener composition has less unpleasant off-taste, aftertaste and/or lingering sweetness as compared to an analogous sweetener composition which does not contain the tri-/tetra-saccharide(s).

In another aspect, the invention relates to a method of modifying, masking, reducing and/or suppressing the unpleasant off-taste, aftertaste or lingering sweetness of at least one sweetener. The method comprises combining the tri-/tetra-saccharide(s) as described above with the at least one sweetener.

As discussed above, the sweetener composition of the invention may also be part of a liquid composition. Consequently, in one embodiment, the present method of the invention also includes the step of dissolving, suspending or dispersing the sweetener(s) and the tri-/tetra-saccharide(s) in a suitable solvent like water or another polar solvent or combination thereof. One or both of the sweetener(s) or the tri-/tetra-saccharide(s) may already be admixed with solvent (e.g., in the form of a syrup or other solution) at the time it is combined with the other component to form the sweetener composition.

Tabletop Sweetener Compositions

In another aspect, the present invention relates to tabletop sweetener compositions comprising the sweetener(s) and tri-/tetra-saccharide(s) as described above and to methods of manufacturing such tabletop sweetener compositions.

As used herein, the term "tabletop sweetener," refers to sweetener compositions that comprise at least one sweetener, and optionally, other ingredients such as bulking agents (in addition to the tri-/tetra-saccharides, which themselves may function as bulking agents, particularly when present in relatively high concentrations), anti-caking agents, flavors, sweetness enhancers and the like, which can be used in the preparation of various food items and/or as an additive to food items. As one example, the tabletop sweetener may be used in the preparation of baked goods or other sweetened foods. As another example, the tabletop sweetener may be used to season, sweeten, or otherwise customize a prepared food item, e.g., beverages, fruit, or yoghurt. In one aspect, the tabletop sweetener is in a crystalline, granulated, or powder form. In various aspects, the tabletop sweetener will comprise one or more sweeteners. In one embodiment, the tabletop sweetener may comprise either or both of at least one caloric sweetener or at least one non-caloric or reduced calorie (as compared to sucrose) sweetener. Typical examples of caloric sweeteners that may be used in tabletop sweeteners include sucrose, fructose, and glucose. Common tabletop forms of these caloric sweeteners include cane sugar, bee sugar, and the like. In recent decades, non-caloric or reduced-caloric sweeteners have gained popularity. In many instances, these sweeteners can be used as substitutes for caloric sweeteners and are often referred to as "sugar substitutes." These sugar substitutes may have sweetness intensities similar to that of sucrose or much higher than that of sucrose (the latter often being referred to as "high intensity" or "high potency" sweeteners).

In many instances, sugar substitutes provide a greater sweetening effect than comparable amounts of caloric sweeteners, such as sucrose or fructose. Therefore, smaller amounts of such sugar substitutes are required to achieve sweetness comparable to that of an amount of sugar. Sugar substitutes, however, typically have a taste profile that differs from sucrose or from fructose. Such differences include, but are not limited to, increased astringency, bitterness, various aftertastes, delayed onset of sweetness, and different mouthfeel. Therefore, sugar substitutes are often formulated with other materials that can provide bulk and can enhance the taste profile to be more similar to that of sucrose or fructose. Thus, sugar substitutes have been formulated to create a tabletop sweetener formulation that has a bulk and a taste profile that is comparable to sucrose or fructose. Nevertheless, consumers can still distinguish the low-calorie sweetener formulations from caloric tabletop sweeteners. Therefore, if low-calorie tabletop sweeteners are to replace caloric tabletop sweeteners, formulations of low-calorie sweeteners must be continuously improved to meet consumer demand.

Thus, there is a need for new tabletop sweetener formulations which are low in calories (or have no calories) containing taste-masking components, which can modify, mask, reduce and/or suppress an unpleasant off-taste, aftertaste or lingering sweetness in the oral cavity left by sugar substitutes not having the disadvantages of known taste-masking substances. In particular, there is a great interest in new tabletop sweetener formulations comprising components having no taste of their own, which do not reduce the sweetening power of the sweetener contained in the tabletop sweetener and in the best case even allow the quantity of sweetener to be reduced. In particular, several or all unpleasant taste impressions including but not limited to bitter, astringent off-taste or aftertaste and/or lingering sweetness should be improved, i.e. reduced or suppressed.

Thus, in another aspect, the invention relates to a tabletop sweetener composition comprising (a) at least one sugar substitute and (b) a taste-masking amount of at least one tri-/tetra-saccharide (e.g., melezitose) as described above. In certain embodiments, the at least one sugar substitute is a high intensity sweetener, which may be natural or synthetic, in particular one or more steviol glycosides such as a rebaudioside, including Stevia extracts such as those comprised predominantly (e.g., at least 50%, at least 60%, at least 70%, at least 80%, at least 90% or at least 95% by weight) of rebaudioside A.

For example, melezitose may be used to reduce the bitter taste of one ore more steviol glycosides such as rebaudioside A in a sweetener composition.

As used herein, a "taste-masking amount" of the tri-/tetra-saccharide(s) as described above means an amount of the tri-/tetra-saccharide(s) as described above (in particular, melezitose) that imparts an improvement in the taste profile of a composition such as a tabletop sweetener composition. As mentioned above, in some instances, for example, the taste-masking may be perceived as a reduction or masking of the bitterness of the sweetener composition, the tabletop sweetener composition or of the beverage or foodstuff containing the sweetener composition. In other instances, for example, the taste masking may also be perceived as an enhancement in the sweetness of the sweetener composition, the tabletop sweetener composition or of the beverage or foodstuff containing the sweetener composition. The taste masking may also be a combination of both bitterness reduction and sweetness enhancement.

In various embodiments, the tabletop sweetener composition as described above comprises the tri-/tetra-saccharide(s) as described above in a taste-masking amount effective to modify, mask, reduce and/or suppress an unpleasant off-taste or aftertaste of the at least one sugar substitute, wherein the taste-masking amount is less than, equal to or greater than a taste threshold concentration associated with the tri-/tetra-saccharide(s).

In other embodiments, the tabletop sweetener composition as described above comprises the tri-/tetra-saccharide(s) as described above in an amount effective to modify, mask, reduce and/or suppress an unpleasant off-taste or aftertaste of a steviol glycoside such as rebaudioside A wherein the amount is less than, equal to or greater than a taste threshold concentration associated with the tri-/tetra-saccharide(s).

The effect(s) of the tri-/tetra-saccharide(s) may remain(s) at least as long as the taste of the sugar substitute is perceived. Tabletop sweetener compositions of the invention may also contain amounts of other ingredients in addition to the tri-/tetra-saccharide(s) and sugar substitute(s), including caloric sweeteners, bulking agents (including bulking agents such as oligo- and poly-saccharides having low or no digestibility and thus low or no caloric content; as previously mentioned, the tri- and tetra-saccharides employed as taste modulators in the present invention may additionally function as bulking agents, especially when present at relatively high levels), anticaking agents, sweetness modifiers, mouthfeel enhancers, flavoring ingredients, and the like. Natural flavors and other natural ingredients are preferred when the product is to be labeled as "all-natural."

In some embodiments, sweetener compositions of the invention provide at least one, if not more than one, of the following desirable characteristics: (a) fewer calories per gram than standard table sugar (sucrose); (b) fewer calories than an amount of standard table sugar perceived as providing comparable sweetness; and (c) lower glycemic index than that of standard table sugar. In some embodiments, the sweetener composition has less than 5 kcal/gram, or less than 3 kcal/gram, or less than 1 kcal/gram. In a typical tabletop sweetener application, for example, the sweetener composition can be packaged in a form where it provides a similar sweetness to 5 to 7 grams of sucrose, while providing fewer than 5 kcal per package.

In another embodiment, tabletop sweetener compositions of the invention contain a plurality of sweetener particles, wherein such particles contain one or more of the ingredients present in the tabletop sweetener composition. Sweetener particles, when present in the tabletop sweetener composition, can have any size suitable for use of the composition as a sweetener. In some embodiments, the average size of the sweetener particles is between 50 microns and 1250 microns, e.g., between 100 microns and 1000 microns. Screening to eliminate particles of undesired sizes can be carried out during the manufacturing process. Thus, in some embodiments, the particle sizes, after screening to eliminate undesired large particles which may be as large as 1500 microns, may vary up to 16 mesh, e.g., up to 14 mesh, or up to 12 mesh, based on the standard United States sieve scale. Further, smaller particle sizes, e.g., 50 mesh, 100 mesh, or 150 mesh, or particles having sizes less than 1 micron, e.g., less than 0.5 microns, may be present with the larger particles. Screening to eliminate particles having sizes less than, for example, 100 mesh or 150 mesh can be carried out if desired. The sweetener composition may be formulated and processed such that the sweetener particles are free-flowing and generally resemble table sugar.

Sweetener particles in the tabletop sweetener composition may or may not have uniform composition. In one embodiment, the particles may be prepared such that they contain a core of a carrier component such as a sugar alcohol, bulking agent or saccharide (which could be, at least in part, a tri-/tetra-saccharide as described above) which is coated with a layer comprised of sugar substitute(s) and, optionally, tri-/tetra-saccharides as described above. In other embodiments, the sweetener particles are uniform in composition; e.g., each particle may be an intimate homogeneous admixture or blend of sugar substitute(s), tri-/tetra-saccharide(s) and other ingredients such as bulking agents which may optionally be part of the sweetener composition. In still other embodiments, the sweetener composition is comprised of particles wherein certain particles contain sugar substitute (and optionally other ingredients) but not tri-/tetra-saccharide and other particles contain tri-/tetra-saccharide (and optionally other ingredients) but not sugar substitute.

Solid sweetener compositions of the invention may have any dissolution rate in water that is suitable for their use as sweeteners. In some embodiments, the sweetener composition can have a dissolution rate in water at 10° C. of between 100 seconds and 200 seconds, e.g., between 125 seconds and 175 seconds, or between 140 seconds and 160 seconds, based on the dissolution of 2 grams of the sweetener composition in 240 ml of water. In some embodiments, the sweetener composition can have a dissolution rate in water at 45° C. of between 50 seconds and 150 seconds, e.g., between 75 seconds and 125 seconds, or between 85 seconds and 110 seconds, based on the dissolution of 2 grams of the sweetener composition in 240 ml of water.

In another embodiment, the invention relates to single-serving packets containing the above-described tabletop sweetener.

Tabletop sweetener compositions of the invention may have any bulk density that is suitable for their use as sweeteners. In some embodiments, the bulk density of the sweetener composition ranges from 0.5 g/cm$^3$ to 1.0 g/cm$^3$, or from 0.7 g/cm$^3$ to 0.8 g/cm$^3$.

A sweetener composition of the invention as described above can be added to any type of consumable product including, but not limited to, food products, beverages, dental products, cosmetic products, pharmaceutical products and animal feed or animal food. The tabletop sweetener compositions of the invention as described above can be added to any consumable products, which are produced in a household or on a small scale. Such consumable products may contain an amount of a natural sugar such as sucrose, glucose or fructose.

Thus, in another aspect, the invention relates to a consumable product composition comprising (a) a consumable product; and (b) tri-/tetra-saccharide(s) as described above.

Thus, in another aspect, the invention relates to a consumable product composition comprising (a) a consumable product; and (b) a sweetener composition as described above.

Thus, in another aspect, the invention relates to a consumable product composition comprising (a) a consumable product; and (b) a tabletop sweetener composition as described above.

The invention, in other aspects, further relates to a consumable product composition as described above, wherein the tri-/tetra-saccharide(s) as described above is/are present in the consumable product composition in an amount effective to modify, mask, reduce and/or suppress an unpleasant off-taste, aftertaste or lingering sweetness of at least one sweetener, a sweetness enhancer or a consumable product, wherein the amount is less than, equal or or greater than a taste threshold concentration associated with the tri-/tetra-saccharide(s).

In certain embodiments where the consumable product is a beverage product in the form of a solution, for example, the concentration of tri-/tetra-saccharide (e.g., melezitose) in the beverage may be at least 4%, at least 5%, at least 6%, at least 7%, at least 8% or at least 9% by weight and/or not more than 15%, not more than 14%, not more than 13%, not more than 12% or not more than 11% by weight. For example, the beverage product may be a solution containing from 5% to 15% by weight melezitose. The beverage product may additionally contain from 50 ppm to 2000 ppm in total of one or more steviol glycosides (e.g., rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M (also known as rebaudioside X), rebaudioside N, rebaudioside O, dulcoside A, dulcoside B, stevioside, steviolmonoside, steviolbioside, rebusoside, glycosylated steviol glycoside(s) and the like and combinations thereof in any proportions). The weight ratio of tri-/tetra-saccharide (e.g., melezitose) to steviol glycoside (e.g., rebaudioside A) may be, for example, from 25:1 to 2000:1, in various embodiments of the present invention.

In one embodiment, the effect(s) of the tri-/tetra-saccharide(s) remain(s) as long as the taste of the sweetener, the sweetness enhancer or the consumable product is perceived.

In various embodiments of the invention, the unpleasant off-taste of the sweetener or the consumable product is at least one of an acidic off-taste, an astringent off-taste, a bitter off-taste, a liquorice off-taste, a metallic off-taste or a throat-burning off-taste. In particular, the unpleasant aftertaste of the sweetener or the consumable product is an astringent or bitter aftertaste.

In other embodiments, the tri-/tetra-saccharide(s) as described above is present in an amount effective to impart rich taste to a consumable product.

In still further embodiments, the sweetener composition of the invention or the tabletop sweetener composition of the invention is present in the consumable in an amount effective to increase a sweetness level of the consumable.

According to certain embodiments, the sweetener composition or the tabletop sweetener composition of the consumable product composition comprises one or more steviol glycosides and/or glucosylated steviol glycosides such as rebaudioside A (wherein the steviol glycoside(s) may be supplied as a *Stevia* extract, a purified *Stevia* extract, a fraction isolated from *Stevia* extract, a highly purified individual steviol glycoside, a *Stevia* extract enriched with one or more purified individual steviol glycosides, a mixture of highly purified individual steviol glycosides, a synthetically or enzymatically prepared or modified steviol glycoside or mixture of synthetically or enzymatically prepared or modified steviol glycosides or the like), in addition to one or more tri- and/or tetra-saccharides as described above (in particular, melezitose), possibly together with one or more additional optional ingredients.

The following exemplary consumable products and their ingredients are suitable for use in embodiments of the present invention.

Consumable products include all food products, including, but not limited to, cereal products, rice products, tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, pharmaceuticals, beverages, carbonated beverages, alcoholic drinks, beers, soft drinks, mineral and aerated waters and other non-alcoholic drinks, fruit drinks, fruit juices, coffee, artificial coffee, tea, cacoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups, concentrates and other preparations for making beverages, and combinations thereof.

Examples of beverages include, but are not limited to, non-alcoholic drinks, water-based, flavored drinks, energy-reduced or with no added sugar, milk- and milk-derivative-based or fruit-juice-based drinks, energy-reduced or with no added sugar; non-alcoholic water-based drinks with added carbon dioxide, sweeteners and flavorings. The present invention may also be employed in the formulation of beverage concentrates or syrups, which are diluted with water, carbonated water or the like prior to consumption.

Consumable products include, without limitation, water-based consumable products, solid dry consumable products, dairy products, dairy-derived products and dairy-alternative products.

In one embodiment, the consumable product is a water-based consumable product selected from the group consisting of beverages, water, near water drinks, aqueous beverages, enhanced/slightly sweetened water drinks, flavored carbonated and still mineral and table waters, non-carbonated beverages, carbonated waters, still waters, soft drinks, carbonated soft drinks, non-alcoholic drinks, alcoholic drinks, beer, wines, liquors, fruit drinks, juice drinks, juices, fruit juices, vegetable juices, nectars, broth drinks, coffee, tea, black tea, green tea, oolong tea, herbal infusions, cacoa (water-based), tea-based drinks, coffee-based drinks, cocao-based drinks, desserts, syrups, frozen fruits, frozen fruit juices, water-based ices, fruit ices, sorbets, dressings, salad dressing, jams, marmalades, canned fruits, savory delicatessen products like delicatessen salads, sauces, ketchup, mustard, pickles and marinated fish, sauces, soups, and beverage botanical materials (whole or ground), or instant powder for reconstitution (coffee beans, ground coffee, instant coffee, cacao beans, cocao powders, instant cocao, tea leaves, instant tea powder).

In another embodiment, the consumable product is a solid dry consumable product selected from the group consisting of cereals, baked food products, biscuits, breads, breakfast cereals, cereal bars, energy bars/nutritional bars, granolas, cakes, rice cakes, cookies, crackers, donuts, muffins, pastries, confectioneries, chewing gum, chocolate products, chocolates, fondants, candies, hard candies, marshmallow, pressed tablets, snack foods, botanical materials (whole or ground), and instant powders for reconstitution.

In another embodiment, the consumable product is a dairy product, dairy-derived product and/or dairy-alternative product selected from the group consisting of milk, fluid milk, cultured milk products, cultured and noncultured dairy-based drinks, cultured milk products cultured with *lactobacillus*, yoghurts, yoghurt-based beverages, smoothies, lassi, milk shakes, acidified milk, acidified milk beverages, butter milk, kefir, milk-based beverages, milk/juice blends, fermented milk beverages, ice cream, desserts, sour cream, dips, salad dressing, cottage cheese, frozen yoghurt, soy milk, rice milk, soy drinks, and rice milk drinks.

In one embodiment, the consumable product is a carbonated drink and the invention relates to a carbonated drink comprising a sweetener composition of the invention or a tabletop sweetener composition of the invention.

In another embodiment, the consumable product is a non-carbonated drink and the invention relates to a non-carbonated drink comprising a sweetener composition of the invention or a tabletop sweetener composition of the invention.

The amount of the sweetener composition in the consumable product of the invention is dependent on the concentration of the natural and/or artificial sweeteners contained therein, the level of sweetness desired in the consumable product as well as on the presence of further auxiliary substances which may, in the absence of the tri-/tetra-saccharide(s) provided by the sweetener composition, affect the taste properties of the consumable product in an adverse or undesirable way.

In another embodiment, the consumable product is a dental product and the invention relates to a dental product comprising a sweetener composition of the invention. Dental products include, but are not limited to toothpaste, dental floss, mouthwash, denture to adhesive, enamel whitener, fluoride treatments and oral care gels. These products are also known in the art.

In another embodiment, the consumable product is a cosmetic product and the invention relates to a cosmetic product comprising a sweetener composition of the invention. Cosmetic products include but are not limited to lipstick, lip balm, lip gloss, and petroleum jelly. These products are also known in the art.

In another embodiment, the consumable product is a pharmaceutical product (medicament) and the invention relates to a pharmaceutical product comprising a sweetener composition of the invention. Pharmaceutical products include but are not limited to over-the-counter and prescription drugs including but not limited to non-tobacco snuff, tobacco substitutes, chewable medications, cough syrups, throat sprays, throat lozenges, cough drops, antibacterial products, pill coatings, gel caplets, soluble fiber preparations, antacids, tablet cores, rapidly absorbed liquid compositions, stable foam compositions, rapidly disintegrating pharmaceutical dosage forms, beverage concentrates for medicinal purposes, aqueous pharmaceutical suspensions, liquid concentrate compositions, and stabilized sorbic acid solutions, phosphate buffers, saline solutions, emulsion, non-aqueous pharmaceutical solvents, aqueous pharmaceutical carriers, solid pharmaceutical carriers, and pharmaceutical preservatives/additives (antimicrobials, antioxidants, chelating agents, inert gases, flavoring agents, coloring agents).

In another embodiment, the consumable product is animal feed or animal food and the invention relates to animal feed or animal food comprising a sweetener composition of the invention.

A conventional beverage may comprise from 20 g/l to 100 g/l standard sugar such as, e.g., sucrose and this standard sugar may achieve a certain desired level of sweetness. It has now been found that by using an inventive sweetener composition comprising a high intensity sweetener to replace at least a portion of this standard sugar, the amount of standard sugar in a beverage can be reduced or eliminated maintaining the same sweetness level, while at the same time masking or reducing unpleasant taste sensations such as bitterness that otherwise (in the absence of the tri-/tetra-saccharide component of the sweetener composition) would arise due to the high intensity.

In another aspect, the invention relates to a method of making a consumable product composition containing an amount of at least one ingredient (such as a high intensity sweetener) having one or more unpleasant taste characteristics (e.g., bitterness), comprising the step of adding to a consumable product one or more of the tri-/tetra-saccharide(s) as described above (e.g., melezitose) to yield a consumable product composition, wherein the consumable product composition has less or substantially no unpleasant off-taste, aftertaste or lingering sweetness. That is, the incorporation of the tri-/saccharide(s) helps to mask or reduce one or more unpleasant taste sensations that would otherwise be detectable in the consumable product composition in the absence of the tri-/tetra-saccharide(s). The ingredient having one or more unpleasant taste characteristics may be a high intensity sweetener or an ingredient other than a high intensity sweetener. More than one such ingredient may be contained in the consumable product composition. The ingredient(s) having one or more unpleasant taste characteristics may be present in the consumable product at the time of combining with the tri-/tetra-saccharides or may be combined with the consumable product after the tri-/tetra-saccharides. The ingredient(s) having one or more unpleasant taste characteristics and the tri-/tetra-saccharides may be combined at the same time with the other components of the consumable product or may be pre-combined (e.g., in the form of a sweetener composition) and then combined with the other components of the consumable product.

In another aspect, the invention relates to a method of providing a sweetener composition, comprising the step of combining with a sweetener the tri-/tetra-saccharide(s) as described above to yield a sweetener composition, wherein the sweetener composition has substantially no unpleasant off-taste, aftertaste or lingering sweetness or has a reduced level of unpleasant off-taste, aftertaste or lingering sweetness when compared to an analogous sweetener which does not contain the tri-/tetra-saccharide(s).

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

Sensory tests were performed to compare the taste of an aqueous solution of rebaudioside A (1000 ppm) (Solution A) with the taste of an aqueous solution of rebaudioside A (250 ppm) and melezitose (10%) (Solution B). The compositions of the solutions were selected so that the solutions were equivalent in sweetness (i.e., the same SEV). The taste of each of the two solutions was rated by a sensory panel as follows:

| Solution | Liking | Off Flavor |
|---|---|---|
| A (Rebaudioside A, 1000 ppm) | 3 | 3 |
| B (Rebaudioside A, 250 ppm, + melezitose, 10%) | 5.3 | 1 |

Solution B (in accordance with the present invention) had a higher (more favorable) "Liking" rating and a lower (better) "Off Flavor" rating than Solution A (containing only rebaudioside A).

Additional sensory testing was carried out in accordance with the following procedure. The general framework for the sensory testing was to compare various concentrations of steviol glycoside (rebaudioside A) ranging from 100 ppm to as high as 2000 ppm at intervals spaced to characterize an adequate dose response. Due to known carryover effects, products were served as no more than two products per day, generally served as one of the following pairs: 100 ppm/250 ppm; 500 ppm/1000 ppm; 750 ppm/1500 ppm; 1000 ppm/2000 ppm. The products were not served counterbalanced, but were instead served in ascending concentration to allow for cleaner reads on both data points. The solutions were served in 2 ounce soufflé cups coded with 3-digit codes at room temperature. Store-purchased distilled water and unsalted crackers were available for the panelists to clear their palates before and during testing. Each daily study targeted 30 persons, though at times as fewer panelists were tested due to exclusionary requirements (i.e., those who are lactating, pregnant, on medication, etc., begin the study but then drop out during the study).

The study was designed as a rating study using an anchored scale of references of sucrose solutions in neutral pH water. In this study, panelists received a series of reference samples labeled and identified with their SEV equivalence. The range exceeded the expected sweetness of the test sample and panelists rated the sweetness using a 15-pt maximum that exceeds the expected sweetness of the test sample.

Prescreening of the test solutions suggested most individuals would perceive these solutions as 10 SEV or less. Because one cannot predict the sensitivities of all individuals effectively prior to testing, a broader range of references was used. Specifically, SEV references were as follows (the percentages stated are in weight %):

2.5 SEV Reference: 2.5% sucrose solution
5.0 SEV Reference: 5.0% sucrose solution
7.5 SEV Reference: 7.5% sucrose solution
10.0 SEV Reference: 10.0% sucrose solution
12.5 SEV Reference: 12.5% sucrose solution Panelists first were asked to familiarize themselves with the intensity of each reference solution and its corresponding SEV. Next, they waited 30 sec and cleansed their palate with water and a cracker. Then panelists were asked to taste the test sample (identified by a random 3-digit code). Then they were instructed to drag a marker on a line scale to match the sweetness of their test samples relative to the references noted above, with the scale ranging from 0 to 15. The value they selected was shown above the line scale so panelists were aware of what values they were indicating. Once this was complete, inquiries related to the liking of the test sample, the similarity of the taste of the test sample to sugar, the intensity of any off flavors, and the identity of any off flavors were asked.

The values used for the liking scale were standard 7-pt hedonic scale ranging from 1 to 7, the similarity scale was a standard 5-pt intensity scale ranging from 1 to 5, and the off flavor scale was a zero-pt anchored 6-pt intensity scale ranging from 0 to 5. The description of the off flavor was open-ended to allow panelists to give any names they would like to potential off notes.

The results obtained are shown in FIGS. 1-6. To begin understanding the impact of a product on the perception of a bittering agent (i.e., an edible ingredient that tastes bitter, such as rebaudioside A), it must be understood how it relates to the impact of sucrose. What is shown in FIG. 1 is how a 2.5% solution of sucrose increases the sweet taste perception of a Reb A (rebaudioside A) dose response curve by about 2.5 sweetness units throughout the dose response. This is exactly what one would expect given that sweetness units are measured relative to percent sucrose.

Figure 2:
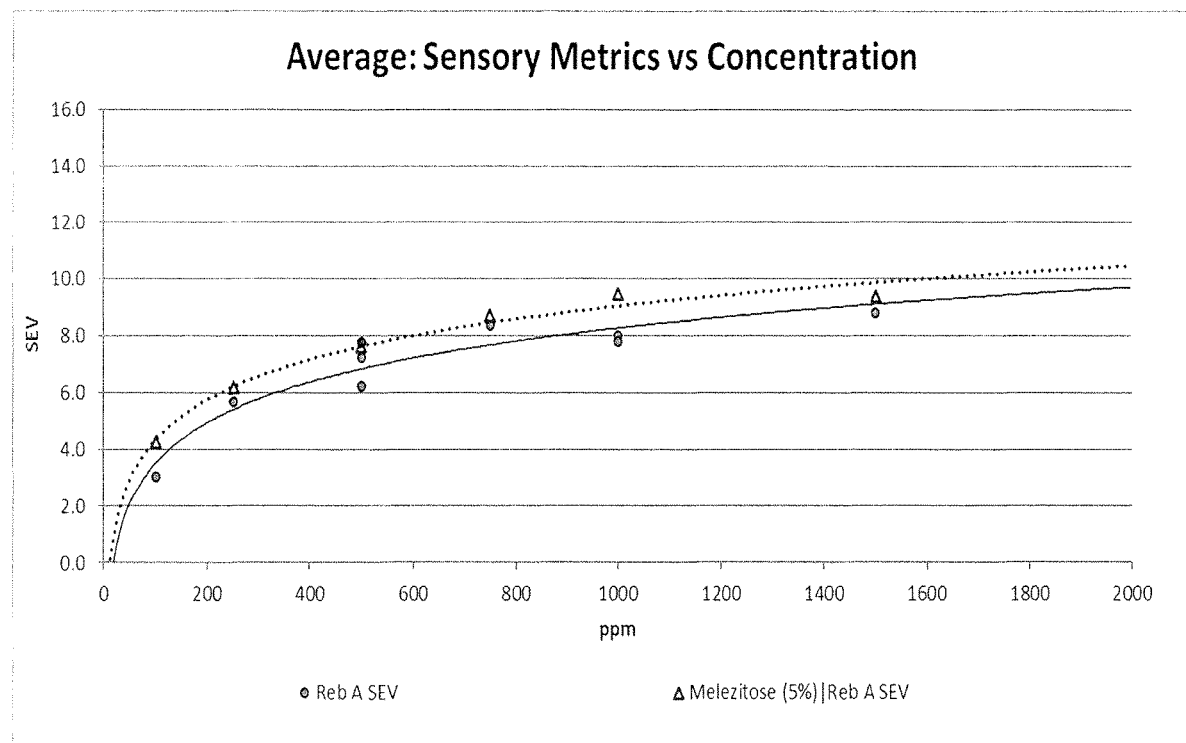

A 5% solution of melezitose is considered to be about as sweet as a 1% solution of sugar, and this is consistently detailed across the dose response curve when Reb A is made in a 5% melezitose solution (FIG. 2). By FEMA GRAS standards, anything below the sweetness equivalency of a 1.5% solution of sucrose is considered below the recognition threshold of sweetness, whereby a person may be able to detect a sensation but may be unable to describe it as "sweet". This is called the area between the detection and recognition thresholds.

Figure 3:
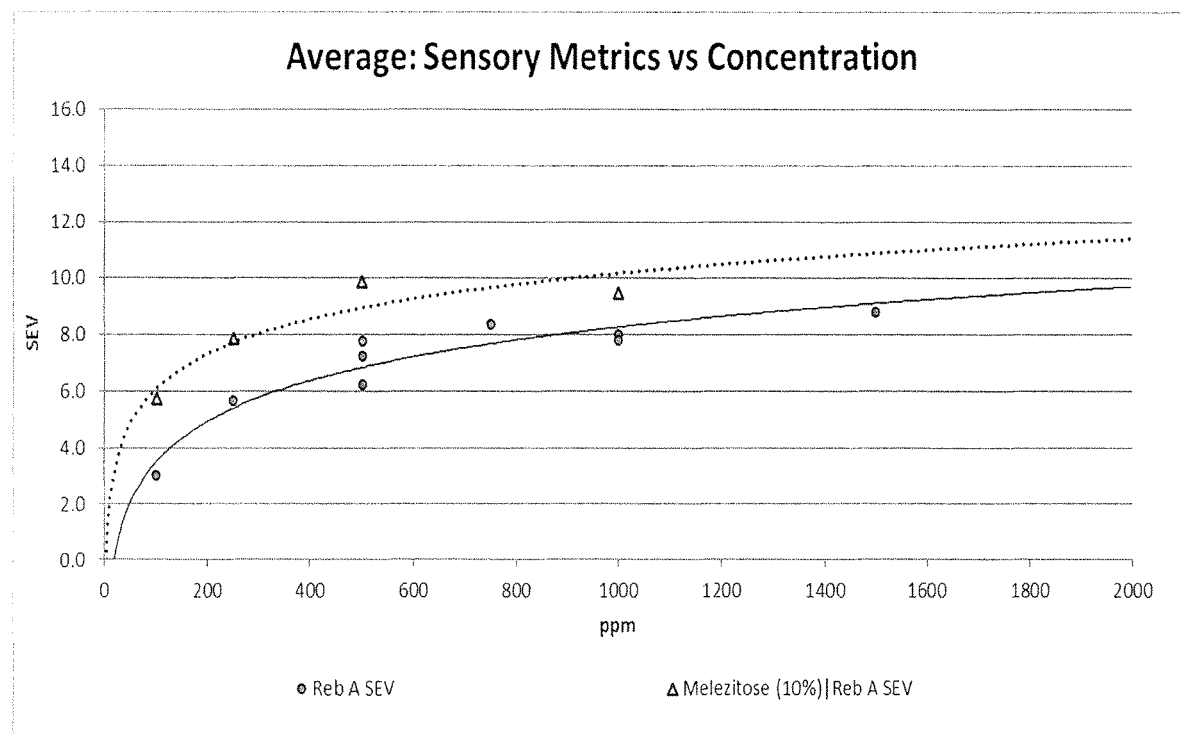

By comparison, a 10% melezitose solution has been shown to be equally sweet as a 2.5% solution of sucrose. This effect is mirrored across the dose response curve of Reb A in a 10% melezitose solution (FIG. 3).

Figure 4:
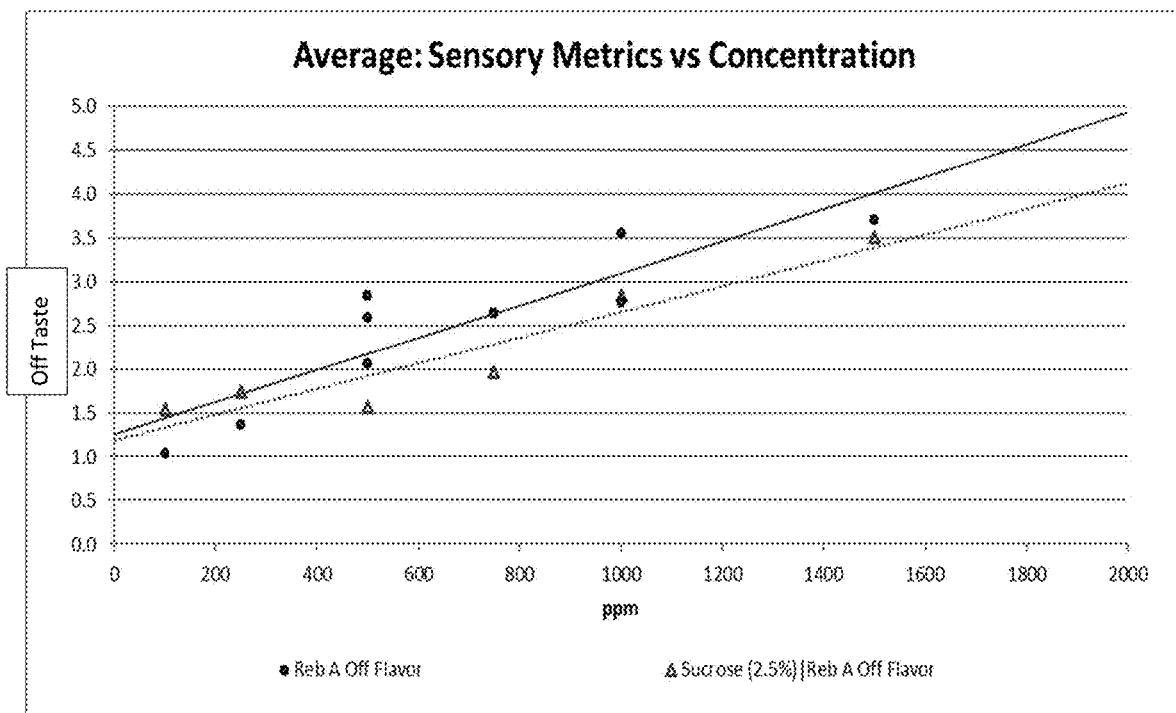

Expanding on this, as the plots in FIG. 4 show, the off flavors of Reb A can be reduced somewhat by a 2.5% solution of sucrose. This effect is largely due to the counterbalancing of sweetness and bitterness, but it is not a masking effect.

Figure 5:
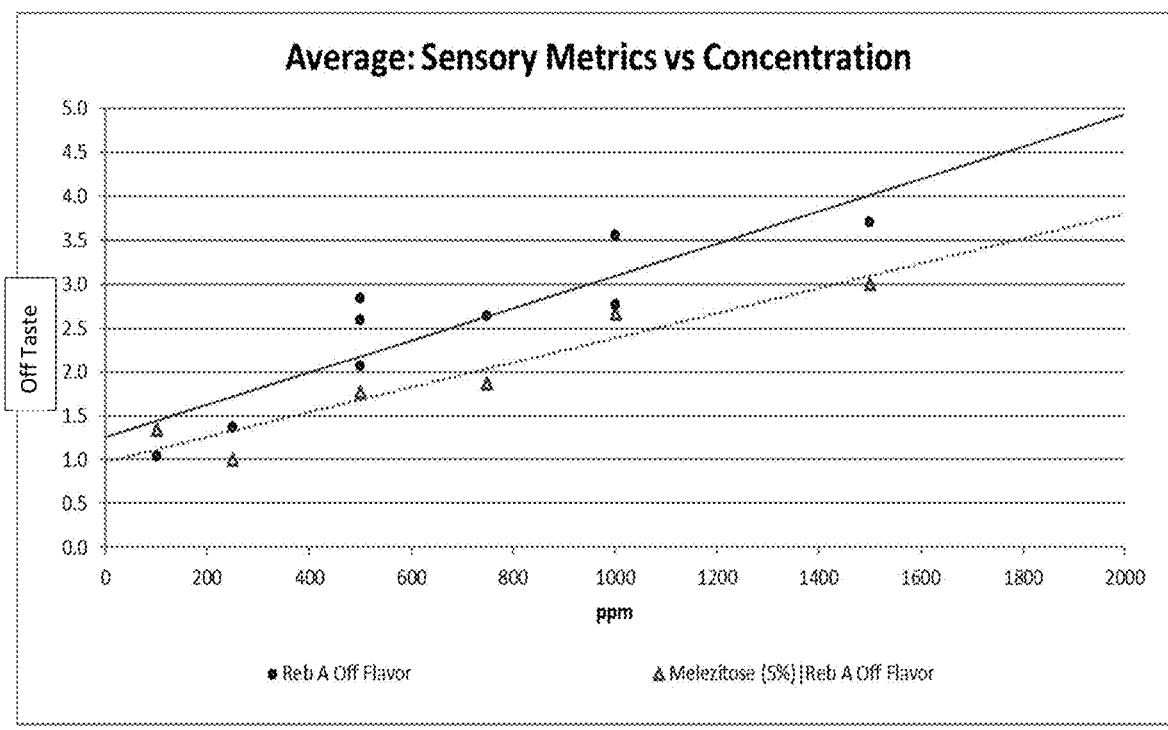
Figure 6:
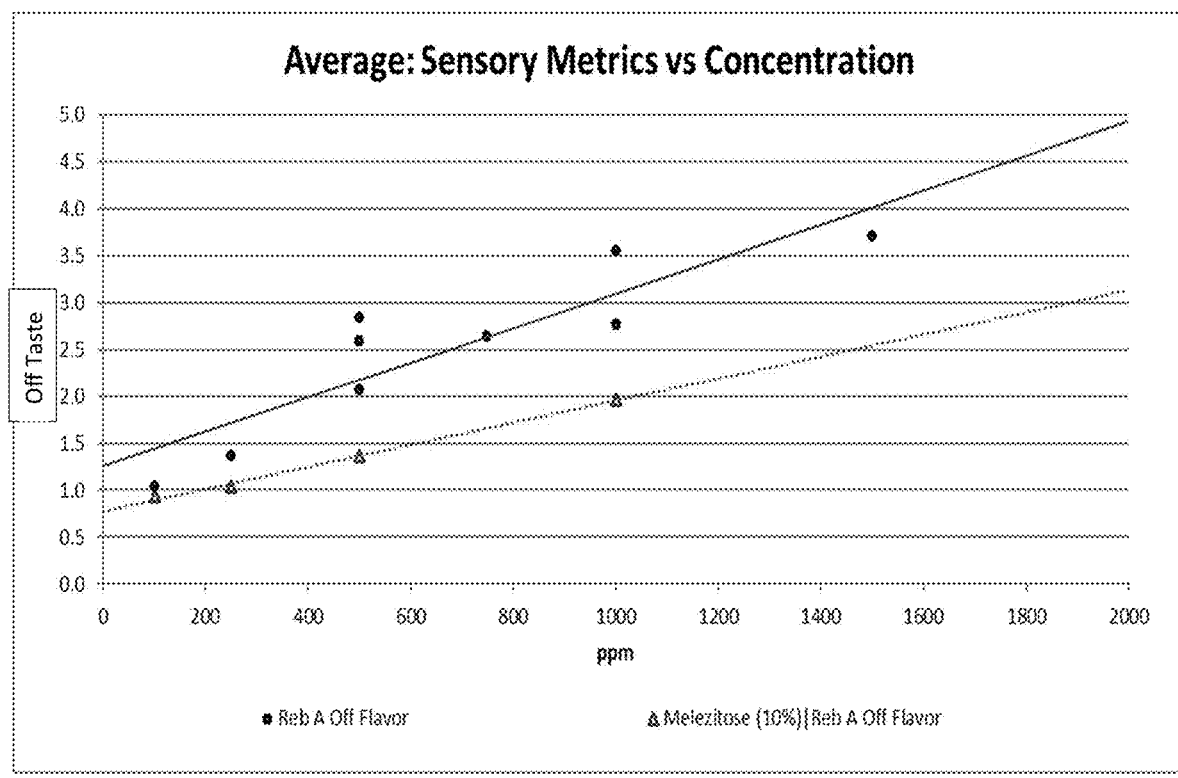

This can be compared with the reduction in off-tastes when using a 5% solution of melezitose (FIG. 5). A 5% solution of melezitose has been shown to be considered subsweet in terms of sweetness threshold, yet it has a clear impact on the reduction of off-tastes.

Taking melezitose concentrations higher (FIG. 6), to match the sweetness of a 2.5% solution of sucrose as noted at a 10% melezitose solution, the level of the reduction in off-tastes is considered dramatic and much more impactful than the equally sweet sucrose solutions can provide.

Example 2

Three aqueous solutions of 1000 ppm rebaudioside A 97 (rebaudioside A having a purity of 97%) were prepared with 10% maltotriose, 2.5% sucrose, or no additional component. The sweetness of a 10% maltotriose solution is approximately equal to a 2.5% sucrose solution. Three panelists were asked to assess the samples for comparative bitterness and were instructed to rinse with water between samples in order to mute any carry-over effects. All three panelists agreed that the sample containing 10% maltotriose was less bitter than the rebaudioside A control. Two of the three panelists found the maltotriose-containing sample to be the least bitter of the three samples provided, with the third panelist stating that the sucrose containing sample was the least bitter. One panelist found the sucrose-containing solution to be the most bitter. These results indicate that maltotriose is effective in masking the bitterness of rebaudioside A 97. The panelist that reported the sucrose-containing solution to be less bitter than the maltotriose containing solution, self-identified as an individual not particularly sensitive to the bitterness of rebaudioside A 97. Therefore, the bitterness masking effect of maltotriose may be more plainly observed in those more sensitive to the bitterness of rebaudioside A 97.

Example 3

Three aqueous solutions of 1000 ppm rebaudioside A 97 were prepared with 10% maltotetraose-enriched syrup (containing 60% maltotetraose on a dry weight basis with other carbohydrates including maltotriose, maltose and glucose), 2.5% sucrose, or no additional component. As a note, the sweetness of a 10% maltotetraose solution is roughly equal to a 2.5% sucrose solution. Three panelists were asked to assess the samples for comparative bitterness and were instructed to rinse with water between samples in order to mute any carry-over effects. Two of the three panelists perceived the sample containing 10% maltotetraose was less bitter than the rebaudioside A control. Two of the three panelists found the maltotetraose containing sample to be the least bitter of the three samples provided, with the third panelist stating that the neat rebaudioside A solution was the least bitter. The other two panelists found the sucrose-containing solution to be equal in bitterness to the neat rebaudioside A solution. These results indicate that maltotetraose is effective in masking the bitterness of rebaudioside A 97. The panelist who reported the neat rebaudioside A solution to be the least bitter commented that the solution was only slightly bitter, indicating that the panelist is not sensitive to rebaudioside A bitterness. Therefore, the bitterness masking effect of maltotetraose may be more plainly observed in those sensitive to the bitterness of rebaudioside A 97.

What is claimed is:

1. A composition for oral ingestion comprising an edible ingredient and melezitose, wherein the edible ingredient comprises Rebaudioside A and has an unpleasant taste sensation when orally ingested in the absence of melezitose and wherein melezitose is present in the composition in a concentration of from 5 wt % to 10 wt % and Rebaudioside A is present in the composition at from 250 ppm wt to 1500 ppm wt, based on the weight of the composition.

2. The composition of claim 1, comprising at least 60% by weight in total of melezitose, and optionally at least one of maltotriose, maltotetraose or a combination thereof, based on the total weight of the melezitose, maltotriose, and maltotetraose.

3. The composition of claim 1, wherein the unpleasant taste sensation is one or more of an unpleasant off-taste, an unpleasant aftertaste, lingering sweetness or bitterness.

4. The composition of claim 1, wherein the unpleasant taste sensation is a bitter taste sensation.

5. The composition of claim 1, wherein the edible ingredient further comprises a high intensity sweetener.

6. The composition of claim 1, wherein the edible ingredient further comprises a high intensity sweetener selected from the group consisting of terpene glycosides, glucosylated steviol glycosides, acesulfame K, saccharin, cyclamate, aspartame, sucralose, neohesperidin dihydrochalcone, and glycyrrhizin.

7. The composition of claim 1, wherein the edible ingredient further comprises a steviol glycoside in addition to the Rebaudioside A.

8. The composition of claim 1, wherein the edible ingredient is selected from the group consisting of xanthines, alkaloids, tannins, polyphenols, quinolone derivatives, limonoids, naringin, phenolic glycosides, flavanoids, flavanoid glycosides, magnesium salts, benzoate salts, neohesperidin, active pharmaceutical ingredients, bitter amino acids and bitter peptides and peptide fragments.

9. The composition of claim 1, wherein the composition is a beverage product.

10. The composition of claim 1, wherein the composition is a beverage product additionally comprising water and at least one flavoring agent.

11. The composition of claim 1, wherein the composition is a beverage product additionally comprising water, at least one flavoring agent and carbonation and having an acidic pH.

12. The composition of claim 1, wherein the composition is a food product.

13. The composition of claim 1, wherein melezitose is present in the composition at a concentration below its taste threshold concentration.

14. The composition of claim 1, wherein melezitose is present in the composition at a concentration at or above its taste threshold concentration.

15. The composition of claim 1, wherein the edible ingredient comprises from 50 ppm to 2000 ppm in total of one or more steviol glycosides in addition to the Rebaudioside A.

16. The composition of claim 1, wherein the composition is a sweetener composition and is comprised of at least one high intensity sweetener in addition to the Rebaudioside A.

17. The composition of claim 1, wherein the composition is a tabletop sweetener composition comprised of at least one bulking agent.

18. A method of reducing or masking an unpleasant taste sensation associated with an edible ingredient comprising from 250 ppm wt to 1500 ppm wt of Rebaudioside A in a composition for oral ingestion, comprising formulating the composition with from 5 wt % to 10 wt % of melezitose, based on the weight of the composition.

19. A method of making a composition for oral ingestion comprised of an edible ingredient comprising from 250 ppm wt to 1500 ppm wt of Rebaudioside A which imparts an unpleasant taste sensation to the composition, the method comprising incorporating in the composition from 5 wt % to 10 wt % of melezitose based on the weight of the composition.

20. The method of claim 19, wherein the melezitose is in the form of a mixture comprised of melezitose and at least one of maltotriose or maltotetraose or a combination of maltotriose and maltotetraose and at least one additional saccharide other than a tri- and/or tetra-saccharide.

21. A method of sweetening a consumable product, comprising formulating the consumable product with the composition of claim 16.

22. The method of claim 18, wherein the unpleasant taste sensation is a bitter taste sensation.

23. The method of claim 19, wherein the unpleasant taste sensation is a bitter taste sensation.

* * * * *